United States Patent [19]

Duemmen

[11] Patent Number: Plant 6,717

[45] Date of Patent: Apr. 4, 1989

[54] GERANIUM PLANT NAMED FEELING

[76] Inventor: Guenter Duemmen, 4134 Rheinberg 4, Dammweg 18-20, Fed. Rep. of Germany

[21] Appl. No.: 110,890

[22] Filed: Oct. 21, 1987

[51] Int. Cl.[4] ..... A01H 5/00
[52] U.S. Cl. ..... Plt./68
[58] Field of Search ..... Plt./68

*Primary Examiner*—Robert E. Bagwill
*Attorney, Agent, or Firm*—Marks Murase & White

[57] ABSTRACT

A new and distinct geranium plant known by the cultivar name Feeling is characterized by a bright lilac colored flower, semi-doubled flower form, white color in the middle of the flower, dark green foliage with good durability under outdoor summer conditions, and a good branching pattern.

1 Drawing Sheet

BACKGROUND OF THE NEW PLANT

The present invention comprises a new and distinct cultivar of geranium, botanically known as *Pelargonium zonale,* hereinafter referred to by the cultivar name Feeling.

Feeling is a product of a planned breeding program which had the objective of creating new geranium cultivars with a bright lilac flower color, semi-doubled flower form.

Feeling was originated from a hybridization made in a controlled breeding program in Rheinberg, FRG, in 1982–83. The female parent was an unnamed seedling. The male parent of Feeling was also an unnamed seedling.

Feeling was discovered and selected as one flowering plant within the progeny of the stated cross by Guenter Duemmen in 1984 in a controlled environment in Rheinberg.

The first act of asexual reproduction of Feeling was accomplished when vegetative cuttings were taken from the initial selection in July 1984 in a controlled environment in Rheinberg by a technician working under formulations established and supervised by Guenter Duemmen. Horticultural examination of selected units initiated July 1984 has demonstrated that the combination of characteristics as herein disclosed for Feeling are firmly fixed and are retained through successive generations of asexual reproduction.

Feeling has not been observed under all possible environmental conditions. The phenotype may vary significantly with variations in environment such as temperature, light intensity, and day length. The following observations, measurements, and comparisons describe plants grown in Rheinberg under greenhouse conditions which approximate those generally used in commercial practice.

The following traits have been repeatedly observed and are determined to be basic characteristics of Feeling which in combination distinguish this geranium as a new and distinct cultivar:

1. Bright lilac flower color;
2. Semi-doubled flower form;
3. White color in the middle of the flower;
4. Dark green foliage with good durability under outdoor summer conditions; and
5. Good branching pattern.

Of the many commercial cultivars known to the present inventors, the most similar in comparison to Feeling is Blues. In comparison to Blues, Feeling has a larger diameter of the corolla, a slighter zonation of the foliage, and a shorter plant height.

The accompanying photographic drawing shows typical flower and foliage characteristics of Feeling, with colors being as true as possible with illustrations of this type.

In the following description color references are made to The Royal Horticultural Society Colour Chart. The color values were determined between 10:00–11:30 a.m. on Sept. 3, 1986 under natural light at Rheinberg in a room with orientation to the north.

Classification:
*Botanical.*—*Pelargonium zonale* cv Feeling.
*Commercial.*—Geranium.

Inflorescence:

A. Umbel:
*Average diameter.*—11 to 13 cm.
*Average depth.*—5 to 7 cm.
*Peduncle length.*—14 to 16 cm.
*Pedicel length.*—2 to 2.5 cm.

B. Corolla:
*Average diameter.*—4 to 4.5 cm.
*Form.*—Semi-double.
*Color (general tonality from a distance of three meters).*—ca. RHS 74 C.
*Color (abaxial).*—ca. RHS 74 C.
*Color (adaxial).*—ca. RHS 74 C to 75 D.

C. Bud:
*Shape.*—Elliptic.
*Color (abaxial).*—ca RHS 57 D.
*Color (adaxial).*—ca. RHS 57 D 56 D.

D. Reproductive organs:
*Androecium.*—Obdiplostemon, centrifugal dedouplement, fertil.
*Gynoecium.*—5-lobed stigma, pubescent, 5 carpels, coenocarp hypogyn.

E. Spring flowering response period:
*FRG.*—50% of plants with at least one flower open 16 weeks after stick of unrooted cuttings.

F. Outdoor flower production: Good.

G. Durability: Good.

Plant

A. Foliage:
*Form.*—Kidney shaped.
*Margin.*—Bicrenated.
*Color (abaxial).*—ca. RHS 139 A to 139 B.
*Color (adaxial).*—ca. RHS 138 B to 137 D.
*Color (zonation).*—ca. RHS 136 A.
*Tolerance of botrytis.*—Good.

B. General appearance and form:
*Internode length.*—Normal.
*Branching pattern.*—Good.
*Height.*—Medium.

I claim:

1. A new and distinct cultivar of geranium known as *Pelargonium zonale,* to be known by the cultivar name Praeludium, as described and illustrated, and particularly characterized by the combination of characteristics of: a bright lilac colored flower; a semi-doubled flower form; white color in the middle of the flower; dark green foliage with good durability under outdoor summer conditions; and a good branching pattern.

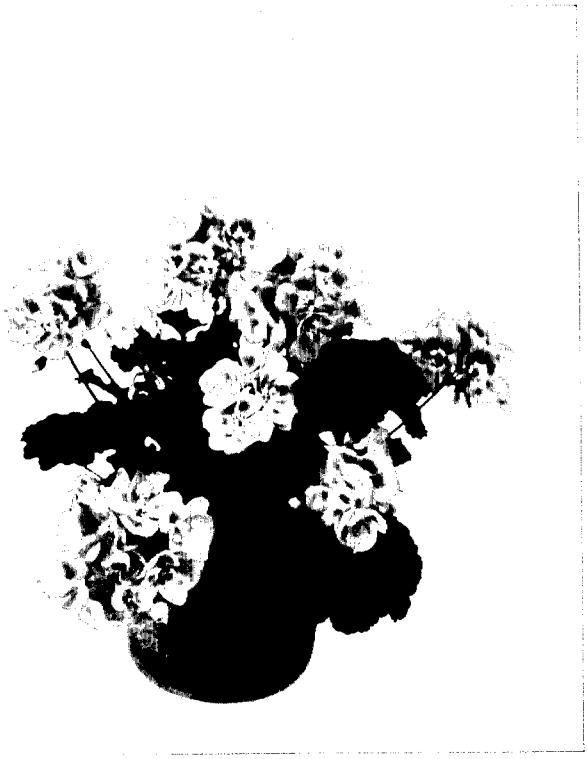

* * * * *